United States Patent [19]

Bremanis et al.

[11] Patent Number: 4,704,403
[45] Date of Patent: Nov. 3, 1987

[54] 3-(2,2,2-TRISUBSTITUTED HYDRAZINIUM) PROPIONATES

[76] Inventors: Gunar A. Bremanis, ulitsa 1905 goda,18, Jurmala; Ivars Y. Kalvinsh, ulitsa Miera,17,kv. 8, Salaspils; Irene B. Antsena, ulitsa Indranu,18,kv. 10, Riga; Edmund Y. Lukevits, ulitsa Ierikju, 43,kv. 10, Riga; Maris M. Veveris, ulitsa Veyavas,10/2,kv. 20, Riga; Marina L. Erenshtein, ulitsa Lielvardes,127,kv. 7, Riga; Valdis D. Mikazhan, ulitsa Talavas,Gatve,5,kv. 40, Riga; Valeryans Y. Kauss, ulitsa Prima,25,kv. 8, Adazhi, Rizhsky raion; Edvard E. Liepinsh, ulitsa Revoljutsivas,85,kv. 22, Riga; Petr T. Trapentsier, ulitsa Fr.Engelsa,40,kv. 24, Riga, all of U.S.S.R.

[21] Appl. No.: 815,296

[22] Filed: Dec. 27, 1985

Related U.S. Application Data

[63] Continuation of Ser. No. 610,631, May 16, 1984, abandoned.

[30] Foreign Application Priority Data

May 18, 1983 [SU] U.S.S.R. ................ 3610211

[51] Int. Cl.[4] ............ C07C 101/74; A01N 37/12
[52] U.S. Cl. ................ 514/554; 514/555; 514/556; 260/501.13
[58] Field of Search ............ 260/501.13; 514/556, 514/554, 555

[56] References Cited

U.S. PATENT DOCUMENTS 4,451,485 5/1984 Kalvinsh et al. ............ 260/501.13
4,481,218 11/1984 Eremeev et al. ............ 260/501.13

FOREIGN PATENT DOCUMENTS 880831 5/1980 Belgium .
2057432 4/1981 United Kingdom .
787995 1/1979 U.S.S.R. .

Primary Examiner—Glennon H. Hollrah
Assistant Examiner—Raymond Covington
Attorney, Agent, or Firm—Burgess, Ryan and Wayne

[57] ABSTRACT

Novel compounds, viz. 3-(2,2,2-trisubstituted hydrazinium) propionates have the following general formula:

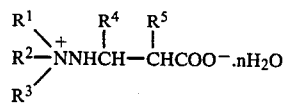

wherein $R^1$, $R^2$ and $R^3$ are an alkyl, a substituted alkyl, a substituted or unsubstituted aryl, an aralkyl or an unsaturated alkyl;
$R^4$, $R^5$ are hydrogen or a lower alkyl; n is 0 to 2, except for the case where $R^1$, $R^2$ and $R^3$ are methyl, $R^4$ and $R^5$ are not hydrogen.

The compounds of the present invention possess both hypotensive and antiarrhythmic activity and are useful in medicine.

9 Claims, No Drawings

3-(2,2,2-TRISUBSTITUTED HYDRAZINIUM) PROPIONATES

This application is a continuation of application Ser. No. 610,631, filed May 16, 1984, now abandoned.

FIELD OF THE INVENTION

The present invention relates to the organic chemistry and, more specifically, to novel compounds, namely 3-(2,2,2-trisubstituted hydrazinium)propionates possessing hypotensive and antiarrhythmic activity and useful in medicine.

BACKGROUND OF THE INVENTION

Known in the art are various compound featuring hypotensive activity which are useful as hypotensive agents such as Niphedipin, Verapamyl, Obzidan and the like. They, however, have but a short-term effect, wherefore their frequent administration becomes necessary.

Also knonw in the art are such antiarrhythmic agents as quinidine and procaine amide. They possess a high toxicity and cause a number of undesirable side effects.

The prior art compound having the structure most resembling that of the compounds according to the present invention, vis. 3-(2,2,2-trimethylhydrazinium)-propionate has a wide spectrum of its biological effect. Known are its growth-stimulating properties in respect of plants and animals, as well as its use for diagnosis of lymphocytic system pathologies (cf. Belgian Pat. No. 880,831; 1980; USSR Inventor's Certificate No. 787995, 1980). The effect of 3-(2,2,2-trimethylhydrazinium)propionate on the cardio-vascular system has not been hitherto described in the literature.

SUMMARY OF THE INVENTION

It is an object of the present invention to provide novel compounds which would have a high hypotensive and antiarrhythmic activity, a protracted effect and a low toxicity.

The compounds according to the present invention, viz. 3-(2,2,2-trisubstituted hydrazinium)propionates are novel and not known from the literature.

This object is accomplished by the novel compounds according to the present invention, namely: 3-(2,2,2-trisubstituted hydrazinium)propionates having the following general formula:

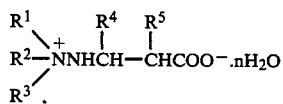

wherein $R^1$, $R^2$ and $R^3$ are each an alkyl, a substituted alkyl, a substituted or unsubstituted aryl, an aralkyl or an unsaturated alkyl; $R^4$ and $R^5$ are hydrogen or a lower alkyl; $n=0$ to 2, except for the case where $R^1$, $R^2$ and $R^3$ are methyl, $R^4$ and $R^5$ are not hydrogen.

DETAILED DESCRIPTION OF THE INVENTION

The compounds according to the present invention are crystalline substances well soluble, in the majority of cases, in water and alcohols.

The study of the biological activity of the compounds according to the present invention has shown that they have a clearly pronounced hypotensive and antiarrhythmic activity.

The study of hypotensive properties of the compounds of this invention has been carried out of hypertensive male rats of the Akamoto-Aoki line aged 25-30 weeks. The animals were divided into groups (7-10 rats in each) and for 2 weeks before the beginning of the experiment they were subjected to an every-day training for adaptation to the unit for measurements of the arterial pressure. The systolic and diastolic arterial pressure were measured indirectly on the tail artery. The level of the arterial pressure prior to administration of the test compounds was measured by way of a triple determination thereof—2 days, one day and right before the administration of the preparation. The compounds were administered intraperitoneally in the form of a 2.5% aqueous solution or a 2.5% suspension in Twin-80 in the dose of 50 mg/kg. The measurement of the arterial pressure was effected 30 minutes, 1, 2, 3 and 4 hours and in some cases 24 hours after the administration of the preparation. For a number of compounds featuring a high efficiency, also determined was the dose causing reduction of the arterial pressure by 30% as compared with the starting level ($ED_{30}$). The statistical processing of the data obtained was carried out using the Student certainty criterion. The data of these experiments are shown in Table 1 hereinbelow.

As it follows from Table 1, the compounds according to the present invention provide a substantial effect of the arterial pressure decrease in the test animals. As compared to the prior art hypotensive preparation—calcium antagonist nifedipine—the compounds according to the present invention feature a protracted effect and in some cases ensure an essential reduction of the arterial pressure even 24 hours after the administration.

The compounds according to the present invention are equally active upon a per os administration ensuring an essential decrease of the arterial pressure spontaneously hypertensive rats of the Akamoto-Aoki line 24 hours after a single-time administration. The respective data are shown in Table 2.

TABLE 1

Variation of the arterial pressure (per cent of the initial value) upon intraperitoneal administration to hypertensive rats in the dose of 50 mg/kg as compared to nifedipine (1 mg/kg intraperitoneally)

| | | Average variation of the arterial pressure (% of the initial) Time after administration | | | | | | | | | |
|---|---|---|---|---|---|---|---|---|---|---|---|
| | | 30 minutes | | 1 hour | | 2 hours | | 4 hours | | 24 hours | |
| Nos 1 | Compound 2 | Systolic 3 | Diastolic 4 | Systolic 5 | Diastolic 6 | Systolic 7 | Diastolic 8 | Systolic 9 | Diastolic 10 | Systolic 11 | Diastolic 12 |
| 1 | 3-(2,2-Dimethyl-2--ethylhydrazinium) propionate monohydrate | −5 | −2 | −11 | −17 | −13 | −22 | −18 | −23 | −18 | −25 |

TABLE 1-continued

Variation of the arterial pressure (per cent of the initial value) upon intraperitoneal administration to hypertensive rats in the dose of 50 mg/kg as compared to nifedipine (1 mg/kg intraperitoneally)

| | | Average variation of the arterial pressure (% of the initial) Time after administration | | | | | | | | |
|---|---|---|---|---|---|---|---|---|---|---|
| | | 30 minutes | | 1 hour | | 2 hours | | 4 hours | | 24 hours | |
| Nos 1 | Compound 2 | Systolic 3 | Diastolic 4 | Systolic 5 | Diastolic 6 | Systolic 7 | Diastolic 8 | Systolic 9 | Diastolic 10 | Systolic 11 | Diastolic 12 |
| 2 | 3-(2,2-Dimethyl-2-allylhydrazinium) propionate | −12 | −10 | −12 | −23 | −18 | −29 | −14 | −31 | −3 | −7 |
| 3 | 3-(2,2-Dimetyl-2-benzylhydrazinium) propionate | −14 | −14 | −14 | −14 | −15 | −21 | −14 | −21 | −9 | −15 |
| 4 | 3-(2,2-Dimethyl-2-naphthylmethyl-hydrazinium) propionate | 0 | 0 | 0 | −3 | −3 | −2 | −5 | −14 | −4 | −7 |
| 5 | 3-(2,2-Dimethyl-2-propargylhydrazinium)propionate hydrogenbromide | −6 | −17 | −10 | −16 | −10 | −7 | −6 | −10 | — | — |
| 6 | 3-(2-Methyl-2,2-diethylhydrazinium) propionate | +4 | +10 | +2 | −4 | 0 | +1 | −6 | −8 | — | — |
| 7 | Nifedipine | −4 | −8 | −12 | −14 | −8 | −21 | −11 | −31 | — | — |

TABLE 2

Study of hypotensive activity of the compounds on spontaneously hypertensive rats at a single peroral administration

| | | Dose mg/kg | Initial | Systolic arterial pressure (mm Hg) Time after administration | | | |
|---|---|---|---|---|---|---|---|
| Nos 1 | Compound 2 | 3 | 4 | 1 hour 5 | 3 hours 6 | 5 hours 7 | 24 hours 8 |
| 1 | 3-(2,2-dimethyl-2-ethylhydrazinium) propionate monohydrate | 40 | 198 | 185(7%) | 190(4%) | 193(3%) | 191(4%) |
| 2 | 3-(2,2-Dimethyl-2-allylhydrazinium) propionate | 50 | 184 | — | 153(17%) | 155(16%) | 170(8%) |
| 3 | 3-(2,2-Dimethyl-2-2 benzylhydrazinium) propionate | 40 | 196 | 155(21%) | 150(23%) | 153(22%) | 168(14%) |

Furthermore, the compounds according to the present invention are far superior, in their activity, to nifedipine upon a repeated peroral administration to rats with spontaneous hypertension of the Akamoto-Aoki line. The data of the corresponding investigation are shown in Table 3 hereinbelow. Thus, after a four-days course of administration (once a day, per os) of the compounds according to the present invention an essential reduction of the arterial pressure in the test animals is observed which is not returned to the initial level even an expiration of four days after discontinuation of the preparation administration, whereas the hypotensive effect of nifedipine is manifested for only 8 hours.

The effect of the compounds according to the present invention on the arterial pressure and vegetative responses has been studied in acute experiments on cats with a mass of 2.8–4.0 kg narcotized by α-glucochloralose (90 mg/kg) and urethane (100 mg/kg intraperitoneally).

TABLE 3

Effect of the compounds of the present invention and nifedipine on the systolic arterial pressure of spontaneously hypertensive rats upon a repeated peroral administration

| | | | Systolic arterial pressure (mm Hg) | | | | | | | | | | |
|---|---|---|---|---|---|---|---|---|---|---|---|---|---|
| | | | 1st day | | 2nd day | | 3rd day | | 4th day | | | | |
| Nos 1 | Compound 2 | Dose, mg/kg 3 | before administration 4 | after administration 5 | before administration 6 | after administration 7 | before administration 8 | after administration 9 | before admin. 10 | after admin. 11 | 5th day 12 | 8th day 13 | 10th day 14 |
| 1 | 3-(2,2-Dimethyl-2-benzylhydrazinium) propionate | 40 | 195.8 | 148.6 (24%) | 167.8 (14%) | — | 153 (22%) | 157.4 (20%) | 156 (20%) | 155 (21%) | 166 (15%) | 157 (20%) | 177.8 (9%) |
| 2 | 3-(2,2-Dimethyl-2-allyl- | 50 | 176.6 | 150.6 (15%) | 166.8 (6%) | 132.8 (25%) | — | 118 (33%) | 129 (27%) | 118.6 (33%) | 126 (29%) | 168 (5%) | 175 (1%) |

TABLE 3-continued

Effect of the compounds of the present invention and nifedipine on the systolic arterial pressure of spontaneously hypertensive rats upon a repeated peroral administration

| | | | Systolic arterial pressure (mm Hg) | | | | | | | | | | |
|---|---|---|---|---|---|---|---|---|---|---|---|---|---|
| | | | 1st day | | 2nd day | | 3rd day | | 4th day | | | | |
| Nos. 1 | Compound 2 | Dose, mg/kg 3 | before administration 4 | after administration 5 | before administration 6 | after administration 7 | before administrat. 8 | after administr. 9 | before admin. 10 | after admin. 11 | 5th day 12 | 8th day 13 | 10th day 14 |
| | hydrazinium) propionate | | | | | | | | | | | | |
| 3 | Nifedipine | | 184.0 | 150.0 (18%) | 186 (1%) | 148 (20%) | 183 (1%) | 153 (17%) | 180 (2%) | 146 (21%) | 178 (3%) | 186 (1%) | 182 (1%) |

The arterial pressure in the common carotid artery, breathing and electrocardiogram of the second standard lead were recorded.

The effect of the compounds according to the present invention on hemodynamic effects of acetylcholine (0.1 μg/kg) neoepinephrine (0.2 μg/kg), noradrenaline (1 μg/kg) and histamine (1.5 μg/kg) was also studied. In some experiments instead of neoepinephrine and noradrenaline adrenaline was used (1 μg/kg). The peripheral part of the vagus nerve was irritated by supromaximum square pulses of the frequency of 30 Hz and duration of 0.1 ms. The results are shown in Table 4.

TABLE 4

Effect of the compounds of the present invention on the arterial pressure and vegetative responses in narcotized animals.

| Nos 1 | Compound 2 | Dose 3 | Variation of arterial pressure, % 4 | Variation of the effect of acetylcholine, % 5 | Hemodynamic effect, % | | |
|---|---|---|---|---|---|---|---|
| | | | | | Noradrenaline 6 | Neoepinephrine 7 | Angiotension 8 |
| 1 | 3-(2,2-Dimethyl-2-allylhydrazinium) propionate | 5 | ±5 | ±0 | ±0 | −20 | −70 |
| 2 | 2-(2,2-Dimethyl-2-hexadecylhydrazinium) propionate | 3 −10 | −5 −3 | ±0 −10 | −15 −80 | −10 −30 | — — |

As it follows from the data of Table 4, the compounds of the present invention provide an essential effect of the responses caused by the administration of biogenic amines, especially angiotensin and noradrenaline, thus lowering reactivity of the organism. This also points to the positive effect of the compounds according to the present invention on the regulation systems of the organism.

The acute toxicity of the compounds according to the present invention was studied on white mice of both sexes with a mass of 20–25 g. A saturated aqueous solution of the compounds or a suspension in Tween-80 was administered to the animals intraperitoneally. The observation over the animals was carried out for 14 days. The results obtained were processed following the Litchfield-Wilkoxon method. As it follows from the data shown in Table 5 hereinbelow, the studied compounds have a very low acute toxicity, thus providing a large spectrum of the therapeutic effect.

TABLE 5

Acute and comparative toxicity of the compounds according to the present invention upon intraperitoneal administration to white mice

| Nos 1 | Compound 2 | Acute toxicity, LD$_{50}$, mg/kg 3 | Relative toxicity with respect to quinidine (LD$_{50}$/ LD$_{50}$ of quinidine) 4 |
|---|---|---|---|
| 1 | 3-(2,2-Dimethyl-2-hexadecylhydrazinium) propionate | 1,450 (906.6–2.175) | 9.3 |
| 2 | 3-(2,2-Dimethyl-2-allylhydrazinium) propionate | 10,594 (8.774–12.792) | 67.9 |
| 3 | 3-(2,2-Dimethyl-2-benzylhydrazinium) propionate | 8,100 (5.785–11.340) | 51.9 |
| 4 | 3-(2,2-Dimethyl-2-ethylhydrazinium) propionate monohydrate | 2,300 (1.643–3.220) | 14.7 |
| 5 | 3-(2,2-Dimethyl-2-propylhydrazinium) propionate | 1,800 (1.125–2.880) | 11.5 |
| 6 | 3-(2,2-Dimethyl-2-napthylmethylhydrazinium) propionate | above 3,000 | above 19.2 |
| 7 | 3-(2,2-Dimethyl-2-phenylethylhydrazinium) propionate | 1,850 (1.294–2.646) | 11.8 |
| 8 | 3-[2,2-Dimethyl-2-(1′,1′-dimethyl-2′-carboxylatoethylhydrazin-1′-ium)-ethylhydrazinium] propionate | 2,100 (1.382–3.192) | 13.4 |
| 9 | 3-(2-Methyl-2,2-diethylhydrazinium) propionate | 1,450 (1.021–2.059) | 9.3 |
| 10 | 3-(2,2,2-Triethylhydrazinium) propionate | above 3,000 | above 19.2 |
| 11 | 3-(2,2-Dimethyl-2-propargylhydrazinium) propionate hydrogen bromide | 1,650 (1.031–2.640) | 10.5 |

TABLE 5-continued

Acute and comparative toxicity of the compounds according to the present invention upon intraperitoneal administration to white mice

| Nos 1 | Compound 2 | Acute toxicity, $LD_{50}$, mg/kg 3 | Relative toxicity with respect to quinidine ($LD_{50}$/$LD_{50}$ of quinidine) 4 |
|---|---|---|---|
| 12 | Quinidine | 156(111.4–218.4) | 1 |
| 13 | Novocainamide | 290(145–580) | 1.85 |

*Average values and their confidential limits at P=0.05.

The antiarrhythmic activity of the compounds according to the present invention was studied on a model of arrhythmia caused by introduction of calcium chloride.

In experiments on white mice with a mass of 18–25 g narcotized with urethane an electrocardiogram was recorded in the second standard lead. A 2% solution of calcium chloride was introduced into the tail vein at a constant rate (0.01 ml for 2 seconds). The dose of calcium chloride causing arrhythmia and the dose causing heart arrest were determined. In experimental groups the test compounds were administered 20–40 minutes prior to the beginning of the experiment intraperitoneally. The results thus obtained are shown in Table 6 hereinbelow.

TABLE 6

Antiarrhythmic activity of the compounds according to the present invention on the model of arrhythmia caused by introduction of calcium chloride (antagonism towards calcium) in experiments on mice

| Nos 1 | Compound 2 | Compound dose, mg/kg intraperitoneally 3 | Dose of calcium chloride causing in the test animals | |
|---|---|---|---|---|
| | | | arrhythmia 4 | heart arrest 5 |
| 1 | 3-(2,2-Dimethyl--2-ethylhydrazinium propionate monohydrate | 5<br>25 | 83.0<br>91.0 | 95.0<br>98.0 |
| 2 | 3-(2,2-Dimethyl-2-hexadecylhydrazinium)propionate | 5<br>25 | 130.5<br>102.7 | 140.6<br>124.5 |
| 3 | 3-(2,2-Dimethyl--2-allylhydrazinium)propionate | 5<br>25 | 99.6<br>95.2 | 118.0<br>103.0 |
| 4 | 3-(2,2-Dimethyl-2-benzylhydrazinium) propionate | 5<br>25 | 90.9<br>111.0 | 103.0<br>112.0 |
| 5 | 3-(2,2-Dimethyl-2-propylhydrazinium) propionate | 5<br>15 | 112.5<br>125.3 | 123.0<br>140.5 |
| 6 | 2-(2,2-Dimethyl-2-naphthylmethylhydrazinium)propionate | 5<br>15 | 108.0<br>126.7 | 132.5<br>143.0 |
| 7 | 3-(2,2-Dimethyl-2-phenylethylhydrazinium) propionate | 5<br>15 | 88.7<br>110.5 | 115.6<br>142.5 |
| 8 | 3-(2,2-Dimethyl-2-(1',1'-dimethyl-2'-carboxylatoethylhydrazin-1'-ium)ethylhydrazinium propionate | 5<br>15 | 96.0<br>108.5 | 112.0<br>120.0 |
| 9 | 3-(2-Methyl-2,2-diethylhydrazinium)propionate | 5<br>15 | 105.5<br>120.0 | 118.6<br>136.0 |
| 10 | 3-(2,2,2-Triethylhydrazinium) propionate | 5<br>15 | 100.0<br>127.0 | 120.0<br>142.5 |
| 11 | 3-(2,2-Dimethyl-2-propargylhydrazinium) propionate hydrogen bromide | 5<br>15 | 110.4<br>120.0 | 125.0<br>135.0 |
| 12 | Control | — | 85.0 | 100.0 |
| 13 | Quinidine | 3<br>10 | 126.9<br>120.8 | 136.0<br>133.5 |
| 14 | Novocainamide | 10<br>30 | 116.0<br>127.0 | 120.0<br>138.0 |

A further study of the antiarrhythmic activity of the compounds according to the present invention was connected with the determination of their effect on experimental arrhythmia induced by adrenaline.

Guinea pigs of both sexes with a mass of 400–700 g were narcotized with urethane (1,500 mg/kg intraperitoneally) The standard second-lead electrocardiogram was recorded. Arrhythmia was caused by a rapid injection (intravenously) of adrenaline in the dose of 50 mg/kg. To find out the protective antiarrhythmia effect of the compounds according to the present invention, the number of animals in which the total number of ectopic contractions was reduced by 50% and more as compared to the control experiments was recorded. The $ED_{50}$ was calculated as the dose of the test compounds which resulted in the appearance of the antiarrhythmic effect in 50% of the experiments. The results obtained in this study of the antiarrhythmic properties of some of the compounds according to the present invention and novocainamide on the adrenaline model of arrhythmia are shown in Table 7. From the data of the Table it follows that the compounds according to the present invention provide a considerable antiarrhythmic effect superior over that of novocainamide.

TABLE 7

Effect of the compounds according to the present invention and hovocainamide on adrenaline-caused arrhythmia in experiments on narcotized guinea pigs

| Compound | Dose, mg/kg intravenously | Efficiency | $ED_{50}$, mg/kg |
|---|---|---|---|
| Novocainamide | 2.5<br>5.0<br>10.0<br>20.0 | 1/5<br>1/5<br>3/5<br>5/5 | 7.6 |
| 3-(2,2-Dimethyl-2-ethylhydrazinium)propionate monohydrate | 3.0<br>10.0<br>20.0 | 1/4<br>2/4<br>4/5 | 8.2 |
| 3-(2,2-Dimethyl-2--phenylethylhydrazinium)propionate | 3.0<br>10.0<br>20.0 | 3/0<br>3/5<br>4/5 | 7.8 |

Therefore, the studies have revealed that the compounds according to the present invention possess a clearly pronounced hypotensive activity and are far more superior in the duration of their effect as compared to nifedipine. The compounds of the present invention are close, as regards the antiarrhythmic activity, to that of quinidine and novocainamide, but they are substantially less toxic and cause no side effects inherent in these preparations. The combination of these properties of the compounds according to the present invention renders them useful in medicine as cardio-vascular agents.

The compounds according to the present invention (3-/2,2,2-trisubstituted hydrazinium/propionates) can be prepared by reacting esters (preferably methyl and ethyl esters) of acrylic, methacrylic, crotonic acids or another α,β-unsaturated carboxylic acid with a corresponding 1,1-disubstituted hydrazine, followed by alkylation of the resulting adduct by a corresponding haloalkyl, haloaralkyl or a halosubstituted unsaturated alkyl derivative into quaternary hydrazinium salts. The desired betaines are recovered by way of a dehalogenating hydrolysis using strong-base anionites or by other conventional methods. The yield of the desired products is up to 90% by weight.

For a better understanding of the present invention some specific examples illustrating the compounds of this invention and the method for preparing same are given hereinbelow.

EXAMPLE 1

To a solution of 73.1 g (0.5 mol) of 3-(2,2-dimethylhydrazino)methylpropionate in 50 ml of ethanol 78.0 g (0.5 mol) of ethyl iodide are added and the mixture is heated at the solvent boiling point for 18 hours. The solvent is removed under a reduced pressure and the residue is crystallized from a mixture of acetone and ethylacetate to give 105.5 g (69.8%) of colourless crystals of 3-(2,2-dimethyl-2-ethylhydrazinium)methylpropionate iodide with the m.p. of 82°–84° C. The recovered crystals are dissolved in 250 ml of ethanol or water and passed through a column with an ion-exchange resin in the OH$^-$ form, the column is washed with 200–300 ml of methanol, the eluates are combined and evaporated to dryness, then treated with dry isopropanol and acetone. The precipitated crystals are filtered-off and crystallized from a mixture of isopropanol and acetone to give 44.5 g (70.5%) of colourless crystals of 3-(2,2-dimethyl-2-ethylhydrazinium)propionate monohydrate, m.p. 182°–185° C. (with decomposition)/from ethanol-methylethylketone).

PMR spectrum (in D$_2$O), δ: 3.13 (2H, t, J=6.4 Hz, CH$_2$N); 2.36 (2H, t, J=6.4 Hz, CH$_2$COO$^-$); 3.24 (6H, s, (CH$_3$)$_2$N$^+$); 1.33 (3H, t, J=6.9 Hz, CH$_3$CH$_2$); 3.56 (2H, qua., J=6.9 Hz, CH$_2$CH$_3$).

Found, %: C 47.45; H 10.08; N 16.01. C$_7$H$_{18}$N$_2$D$_3$1H$_2$O. Calculated, %: C 47.17; H 10.18; N 15.72.

EXAMPLE 2

To a solution of 73.1 g (0.5 mol) of 3-(2,2-dimethylhydrazino)methylpropionate in 50 ml of ethanol 85.0 g (0.5 mol) of propyl iodide are added and heated at the boiling point of the solvent for 18 hours. The solvent is distilled-off to give 112.56 g (71.2%) of colourless crystals of 3-(2,2-dimethyl-2-propylhydrazinium)methylpropionate iodide with the melting point of 68°–70° C. (from a mixture of acetone and ethylacetate).

The recovered crystals are dissolved in 250 ml of methanol or water and further treated as described in the foregoing Example 1 to give 55.45 g (89.4%) of 3-(2,2-dimethyl-2-propylhydrazinium)propionate, m.p. 188°–193° C. (with decomposition) (from n-butanol-methylethylketone).

PMR spectrum (in D$_2$O), δ: (3.14 (2H, t, J=6.4 Hz, CH$_2$N); 2.36 (2H, t, J=6.4 Hz, CH$_2$COO$^-$); 3.22 (6H, s, (CH$_3$O$_2$N$^+$); 3.44 (2H, m, N$^+$CH$_2$CH$_2$CH$_3$); 1.8 (2H, m, CH$_2$CH$_2$CH$_3$); 0.96 (3H, m, CH$_2$CH$_2$CH$_3$).

Found, %: C 54.97; H 10.64; N 15.93. C$_8$H$_{18}$N$_2$O$_2$. Calculated, %: C 55.14; H 10.41; N 16.08.

EXAMPLE 3

To a solution of 73.1 g (0.5 mol) of 3-(2,2-dimethylhydrazino)methylpropionate in 50 ml of ethanol 152.68 g (0.5 mol) of hexadecyl bromide are added and heated at the boiling temperature of the solvent for 18 hours. The solvent is removed under a reduced pressure to give 185.8 g (82.3%) of an oil.

The recovered product is treated further as described in Example 1 hereinbefore to give 58.69 g (40.2%) of 3-(2,2-dimethyl-2-hexadecylhydrazinium)propionate in the form of colourless crystals with the melting temperature of 100°–102° C. (from tetrahydrofuran).

PMR spectrum (in DMSO-d$_6$): 3.17 (2H, CH$_2$N); 2.51 (2H, COO$^-$) 3.33 (9H, s, (CH$_3$)$_3$N$^+$); 0.7–1.4 (33H, (CH$_2$)$_{15}$CH$_3$).

Found, % C 70.45; H 12.29; N 7.62; C$_{21}$H$_{24}$N$_2$O$_2$. Calculated, %: C 70.73; H 12.44; N 7.86.

EXAMPLE 4

To a solution of 73.1 g (0.5 mol) of 3-(2,2-dimethylhydrazino)methylpropionate in 50 ml of ethanol 60.49 g (0.5 mol) of allyl bromide are added and heated at the boiling temperature of the solvent for 2 hours. The solvent is removed under a reduced pressure to give 99.39 g (74.4%) of colourless crystals melting at 95°–96° C. (from acetone).

The recovered product is further treated in a manner similar to that described in Example 1 to give 61.42 g (91.1%) of 3-(2,2-dimethyl-2-allylhydrazinium)propionate semihydrate in the form of colourless crystals with the m.p. of 158°–160° C. (from isopropanol-methylethylketone).

PMR spectrum (in D$_2$O), δ: 3.22 (2H, t, J=6.4 Hz, CH$_2$N); 2.36 (2H, t, J=6.4 Hz, CH$_2$COO$^-$); 3.26; (6H, s, (CH$_3$)$_2$N$^+$); 4.11 (2H, m, CH$_2$—CH=CH$_2$); 5.6–6.0 (3H, m, CH$_2$CH=CH$_2$).

Found, %: C 53.25; H 9.50; N 15.24; C$_8$H$_{16}$N$_2$O$_2$½ H$_2$O. Calculated, %: C 53.02; H 9.46; N 15.46.

EXAMPLE 5

To a solution of 73.1 g (0.5 mol) of 3-(2,2-dimethylhydrazino)propionate in 50 ml of ethanol 63.30 g (0.5 mol) of benzyl chloride are added and heated at the boiling temperature of the solvent for 18 hours. The solvent is removed under a reduced pressure to give 114.96 g (84.3%) of colourless crystals with the melting point of 130°–131° C. (from acetone-methylethylketone).

The recovered product is further treated as described in Example 1 hereinbefore to give 72.24 g (77.1%) of 3-(2,2-dimethyl-2-benzylhydrazinium)propionate in the form of colourless crystals melting at 180°–182° C. (from ethanol-acetone).

PMR spectrum (in D$_2$O): δ3.30 (2H, t, J=6.5 Hz, CH$_2$N); 2.38 (2H, t, J=6.5 Hz, CH$_2$COO$^-$); 3.22 (6H, s, (CH$_3$)$_2$N$^+$); 4.67 (2H, s, CH$_2$Ph); 7.56 (5H, C$_6$H$_5$).

Found, %: C 64.56; H 8.29; N 12.51 C$_{12}$H$_{18}$N$_2$O$_2$. Calculated, %: C 64.86; H 8.16; N 12.60.

EXAMPLE 6

To a solution of 73.1 g (0.5 mol) of 3-(2,2,-dimethylhydrazino)methylpropionate in 50 ml of ethanol 88.33 g (0.5 mol) of α-(chloromethyl)naphthalene are added and heated at the boiling temperature of the solvent for 18 hours. The solvent is removed under a reduced pressure to give 116.86 g (72.4%) of colourless crystals with the melting point of 193°–194° C. (from acetone-methylethylketone-ethylacetate).

The recovered product is further processed as described in Example 1 to give 51.07 g (51.8%) of colourless crystals of 3-(2,2-dimethyl-2-naphthylmethylhydrazinium)propionate melting at 204°–205° C. (from ethanol).

PMR spectrum (in $D_2O$), δ: 3.31 (2H, t, J=6.2 Hz, $CH_2N$); 2.44 (2H, t, J=6.2 Hz, $CH_2COO^-$); 3.18 (6H, s, $(CH_3)_2N^+$); 4.89 (2H, s, $\underline{CH_2}$-naphthyl); 7.5–8.1 (7H, aromatic protons).

Found, %: C 70.29; H 7.63; N 10.03. $C_{16}H_{20}N_2O_2$. Calculated, %: C 70.56; H 7.40; N 10.29.

EXAMPLE 7

To a solution of 73.1 g (0.5 mol) of 3-(2,2-dimethylhydrazino)methylpropionate in 50 ml of acetone 92.54 g (0.5 mol) of β-phenylethylbromide are added and heated at the boiling temperature of the solvent for 18 hours. The solvent is removed under a reduced pressure to give 94.9 g (57.3%) of colourless crystals with the melting point of 144°–145° C. (from acetone-ethylacetate).

The recovered product is further treated as described in Example 1 to give 56.41 g (72.3%) of colourless crystals of 3-(2,2-dimethyl-2-phenylethylhydrazinium)propionate dihydrate melting at 164°–167° C. (from methanol-acetone).

PMR spectrum (in $D_2O$), δ: 3.22 (2H, t, 6.4 Hz, $CH_2N$); 2.38 (2H, t, J=6.4 Hz, $CH_2COO^-$); 3.33 (6H, s, $(CH_3)_2N^+$); 3.76 (2H, $PhCH_2\underline{CH_2}N^+$), 3.16 (2H, $Ph\underline{CH_2}CH_2N^+$), 7.36 (5H, $C_6H_5$).

Found, %: C 57.43; H 8.68; N 10.35. $C_{13}H_{20}N_2O_2$2-$H_2O$. Calculated, %: C 57.33; H 8.38; N 10.29.

EXAMPLE 8

To a solution of 73.1 g (0.5 mol) of 3-(2,2-dimethylhydrazino)methylpropionate in 50 ml of ethanol 46.97 g (0.25 mol) of dibromoethane are added and heated at the boiling point of the solvent for 18 hours. The solvent is removed under a reduced pressure to give 173.37 g (72.2%) of colourless crystals with the melting temperature of 165°–168° C. (from ethanol-methylethylketone).

The recovered product is further treated as described in Example 1 to give 10.25 g (8.7%) of 3-(2,2-dimethyl-2-[1',1'-dimethyl-2'-carboxylatoethylhydrazin-1'-ium]-ethylhydrazinium)propionate dihydrate in the form of colourless crystals melting at 223°–225° C. (from ethanol-acetone).

PMR spectrum (in $D_2O$): δ2.89 (4H, t, J=6.7 Hz, $CH_2N$); 1.89 (4H, t, J=6.7 Hz, $CH_2COO^-$); 3.13 (6H, s, $(CH_3)_2N^+$); 4.00 (4H, $N^+CH_2CH_2N^+$).

Found, %: C 44.15; H 9.18; N 16.90. $C_{12}H_{26}N_4O_4$2-$H_2O$. Calculated, %: C 44.16; H 9.26; N 17.17.

EXAMPLE 9

To a solution of 87.1 g (0.5 mol) of 3-(2,2-diethylhydrazino)propionate in 50 ml of ethanol 70.97 (0.5 mol) of methyl iodide are added and heated at the solvent boiling temperature for 18 hours.

The solvent is removed under a reduced pressure to give 108.60 g (68.7%) of colourless crystals (melting point of 78°–79° C. (from isopropanol).

The recovered product is further treated as described in Example 1 to give 49.07 g (74.3%) of colourless crystals of 3-(2-methyl-2,2-diethylhydrazinium)propionate monohydrate melting at 77°–79° C. (from ethanol-methylethylketone).

PMR spectrum (in $D_2O$): δ3.07 (2H, t, J=6.3 Hz, $CH_2N$); 2.33 (2H, t, J=6.3 Hz, $CH_2COO^-$); 3.10 (3H, s, $CH_3N^+$), 1.31 (6H, t, J=6.9 Hz $(\underline{CH_3}CH_2)N^+$); 3.48 (4H, quad., J=6.9 Hz, $(CH_3\underline{CH_2})_2N^+$).

Found, %: C 50.00; H 10.54; N 15.44. $C_8H_{18}N_2O_2$1-$H_2O$. Calculated, %: C 49.98; H 10.49; N 14.57.

EXAMPLE 10

To a solution of 87.1 g (0.5 mol) of 3-(2,2-diethylhydrazino)propionate in 50 ml of ethanol 77.98 g (0.5 mol) of ethyl iodide are added and heated at the boiling point of the solvent for 18 hours. The solvent is removed under a reduced pressure to give 117.88 g (71.4%) of colourless crystals melting at 102°–103° C. (from isopropanol).

The recovered product is further treated as described in Example 1 to give 58.92 g (80%) of colourless crystals of 3-(2,2,2-triethylhydrazinium)propionate monohydrate melting at 173°–176° C.

PMR spectrum (in $D_2O$): δ3.08 (2H, t, J=6.3 Hz, $CH_2N$); 2.38 (2H, t, J=6.3 Hz, $CH_2COO^-$); 3.46 (6H, quad., J=6.9 Hz, $N^+(CH_2CH_3)_3$); 1.30 (9H, t, J=6.9 Hz, $N^+(CH_2CH_3)_3$).

Found, %: C 52.28; H 10.92; N 13.30. $C_9H_{20}N_2O_2$1-$H_2O$. Calculated, %: C 52.40; H 10.75; N 13.58.

EXAMPLE 11

To a solution of 73.1 g (0.5 mol) of 3-(2,2-dimethylhydrazino)methylpropionate in 50 ml of ethanol 59.48 g (0.5 mol) of propargyl bromide are added and heated at the solvent boiling point for 10 hours. The solvent is removed under a reduced pressure to give 64.17 g (48.4%) of a yellowish oil.

The recovered product is dissolved in water, acidified with concentrated HBr and boiled for 10 minutes. The solvent is removed under a reduced pressure to give 31.97 g (52.6%) of 3-(2,2-dimethyl-2-propargylhydrazinium)propionate hydrogen bromide in the form of colourless crystals melting at 127°–128° C. (from ethanol).

PMR spectrum (in $D_2O$): δ3.31 (2H, t, J=6.4 Hz, $CH_2N$); 2.63 (2H, t, J=6.4 Hz, $CH_2COO^-$); 3.40 (6H, s, $(CH_3)_2N^+$); 5.08 (2H, $\underline{CH_2}-C\equiv CH$); 3.27 (1H, $CH_2-C\equiv\underline{CH}$).

Found, %: C 37.99; H 6.10; N 11.41. $C_8H_{15}N_2O_2Br$. Calculated, %: C 38.26; H 6.02; N 11.16.

EXAMPLE 12

To a solution of 73.1 g (0.5 mol) of 3-(2,2-dimethylhydrazino)methylpropionate in 50 ml of ethanol 85.0 g (0.5 mol) of isopropyl iodide are added and heated at the solvent boiling point for 18 hours.

The solvent is removed under a reduced pressure to give 115.59 g (68.0%) of colourless crystals melting at 74.5°–75.5° C. (from a mixture of acetone and ethylacetate).

The recovered product is further treated as described in Example 1 to give 43.33 g (60.6%) of colourless crystals of 3-(2,2-dimethyl-2-isopropylhydrazinium)propionate dihydrate melting at 188°–191° C. (from ethanol-acetone).

PMR spectrum (in $D_2O$): δ3.14 (2H, dd, J=5.9 Hz, $CH_2N$); 2.34 (2H, dd, J=5.9 Hz, $CH_2COO^-$); 3.15 (6H, s $(CH_2)_2N^+$); 3.92 (1H, m, $\underline{CH}$); 1.39 (6H, d, J=6.6 Hz, $CH(CH_3)_2$).

Found, %: C 45.81; H 10.44; N 13.02; $C_8H_{18}N_2O_2 \cdot 2H_2O$. Calculated, %: C 45.70; H 10.55; N 13.32.

EXAMPLE 13

To a solution of 73.1 g (0.5 mol) of 3-(2,2-dimethylhydrazino)methylpropionate in 50 ml of ethanol 82.54 g (0.5 mol) of n-hexyl bromide are added and heated at the solvent boiling temperature for 18 hours to give 103.96 g (66.8%) of colourless crystals melting at 75°–76° C. (from a mixture of acetone-ethylacetate).

The recovered product is further treated as described in Example 1 to give 39.76 g (50.8%) of colourless crystals of 3-(2,2-dimethyl-2-hexylhydrazinium)propionate monohydrate melting at 185° C. (with decomposition) (from ethanol-methylethylketone).

PMR spectrum (in $D_2O$): $\delta 3.11$ (2H, dd, J=5.8 Hz, $CH_2NH$); 2.33 (2H, dd, J=5.8 Hz, $CH_2COO^-$); 3.21 (6H, s, $(CH_3)_2N^+$); 3.49 (2H, m, α—$CH_2$); 1.76 (2H, β—$CH_2$); 1.5 (2H, m, γ—$CH_2$); 0.83 (3H, s, $CH_3$).

Found, %: C 56.05; H 11.03; N 11.70. $C_{11}H_{24}N_2O_2 \cdot 1\text{-}H_2O$. Calculated, %: C 56.38; H 11.18; N 11.95.

EXAMPLE 14

To a solution of 73.1 g (0.5 mol) of 3-(2,2-dimethylhydrazino)methylpropionate in 50 ml of ethanol 85.98 g (0.5 mol) of β-hydroxyethyl iodide are added and heated at the solvent boiling point for 6 hours. The solvent is removed under a reduced pressure to give 129.17 g (81.2%) of an oil. The recovered product is further treated as described in Example 1 to give 41.59 g (48.3%) of colourless crystals of 3-(2,2-dimethyl-2-hydroxyethylhydrazinium)propionate dihydrate melting at 208°–212° C. (from isopropanol-acetone).

PMR spectrum (in $D_2O$): $\delta 3.16$ (2H, dd, J=6.0 Hz, $CH_2NH$); 2.36 (2H, dd, J=6.0 Hz, $CH_2COO^-$); 3.33 (6H, s, $(CH_3)_2N^+$); 3.67 (2H, m, $CH_2N$); 4.04 (2H, m, $OCH_2$);

Found, %: C 39.25; H 9.20; N 13.18. $C_7H_{16}N_2O_3 \cdot 2H_2O$. Calculated, %: C 39.61; H 9.50; N 13.20.

EXAMPLE 15

To a solution of 79.1 g (0.5 mol) of 2-methyl-3-(2,2-dimethylhydrazino)-methylpropionate in 50 ml of ethanol 70.97 g (0.5 mol) of methyl iodide are added and heated at the solvent boiling temperature for 18 hours to give 116.32 g (77.0%) of colourless crystals melting at 115°–116° C. (from isopropanol).

The recovered product is further treated as described in Example 1 to give 65.94 g (96.1%) of colourless crystals of 3-(2,2,2-trimethylhydrozinium)-2-methylpropionate monohydrate melting at 166°–167° C. (from a mixture of ethanol and methylethylketone).

MPR spectrum (in $D_2O$), δ: 2.96 and 3.11 (2H, m, J=4.0 and 8.1 Hz, $CH_2NH$); 2.37 (1H, m, CH, J=6.6 Hz and 12.0 Hz); 1.12 (3H, d, J=6.6 Hz, $CH_3$—CH); 3.27 (9H, s, $(CH_3)_3N^+$).

Found, %: C 47.02; H 10.11; N 15.35. $C_7H_{16}N_2O_2 \cdot 1\text{-}H_2O$. Calculated, %: C 47.17; H 10.18; N 15.72.

What is claimed is:

1. 3-(2,2,2-Trisubstituted hydrazinium)propionates of the general formula:

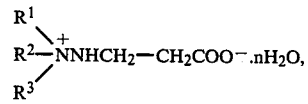

wherein $R^1$, $R^2$, $R^3$ are each an alkyl, a hydrocarbon substituted alkyl, a hydrocarbon substituted or an unsubstituted aryl, an aralkyl, or an unsaturated alkyl of up to 16 carbon atoms, with the proviso that at least one of $R^1$, $R^2$ and $R^3$ contains from 3 to 16 carbon atoms.

2. The compound according to claim 1 wherein $R^1$ is alkyl, β-hydroxyethyl, benzyl, β-phenylethyl, naphthylmethyl, allyl, propargyl, 1',1'-dimethyl-2'-carboxylatoethylhydrazin-1'-ium; $R^2$ and $R^3$ are methyl or ethyl; provided that at least one of $R^1$, $R^2$ and $R^3$ contains from 3 to 16 carbon atoms.

3. The compound according to claim 1 wherein $R^1$ is benzyl, naphthylmethyl, allyl or propargyl and $R^2$ and $R^3$ are methyl.

4. A pharmaceutical composition possessing hypotensive and and antiarrhythmic activity comprised of a pharmaceutically acceptable carrier and a pharmaceutically effective amount of the compound of claim 1.

5. A pharmaceutical composition possessing hypotensive and and antiarrhythmic activity comprised of a pharmaceutically acceptable carrier and a pharmaceutically effective amount of the compound of claim 2.

6. A pharmaceutical composition possessing hypotensive and and antiarrhythmic activity comprised of a pharmaceutically acceptable carrier and a pharmaceutically effective amount of the compound of claim 3.

7. A process for controlling arrhythmic activity which comprises administering a pharmaceutically effective amount of the composition of claim 4.

8. A process for controlling arrhythmic activity which comprises administering a pharmaceutically effective amount of the composition of claim 5.

9. A process for controlling arrhythmic activity which comprises administering a pharmaceutically effective amount of the composition of claim 6.

* * * * *